United States Patent [19]

Bonor et al.

[11] 4,264,506

[45] Apr. 28, 1981

[54] PROCESS FOR PREPARING ARALKYL DERIVATIVES OF XANTHENE COMPOUNDS

[75] Inventors: Alan L. Bonor, Framingham; James W. Foley; Louis Cincotta, both of Andover, all of Mass.

[73] Assignee: Polaroid Corporation, Cambridge, Mass.

[21] Appl. No.: 33,002

[22] Filed: Apr. 24, 1979

[51] Int. Cl.³ ............................................. C07D 311/82
[52] U.S. Cl. ..................................................... 260/336
[58] Field of Search ............................................ 260/336

[56] References Cited

U.S. PATENT DOCUMENTS

| | | | |
|---|---|---|---|
| 2,937,186 | 5/1960 | Burckhalter et al. | 260/336 |
| 3,901,918 | 8/1975 | Koga et al. | 260/335 |

FOREIGN PATENT DOCUMENTS 2504925  8/1976  Fed. Rep. of Germany .
744972  2/1956  United Kingdom .

OTHER PUBLICATIONS

Beilstein, vol. 12, p. 180 (1929).

*Primary Examiner*—Norma S. Milestone
*Attorney, Agent, or Firm*—Gaetano D. Maccarone

[57] ABSTRACT

There is described a process for preparing aralkyl derivatives of xanthene dyes wherein and now abandoned the xanthene dye is initially reacted with a strong base such as an alkali metal hydroxide to form a salt of the dye which is then reacted with an aralkyl compound to form the aralkylated xanthene dye.

15 Claims, No Drawings

PROCESS FOR PREPARING ARALKYL DERIVATIVES OF XANTHENE COMPOUNDS

CROSS-REFERENCE TO RELATED CASES

Reference is made to copending application Ser. No. 32,881, filed on even date herewith and now abandoned.

BACKGROUND OF THE INVENTION

This application is drawn to a process for forming aralkyl derivatives of xanthene dyes and, more particularly, to such a process wherein a previously formed xanthene dye is aralkylated.

Multicolor images formed in accordance with the principles of subtractive color photography employ yellow, magenta and cyan image forming dyes. The yellow dye ideally transmits only green and red light and absorbs only blue light and thus is sometimes referred to as "minus blue". In like manner, the magenta ("minus green") dye ideally absorbs only green light and transmits only red and blue light, and the cyan ("minus red") dye ideally absorbs only red light and transmits only green and blue light. Unfortunately, the dyes which are available for use in subtractive color photography are not "ideal" dyes but rather, tend to absorb some of the light that they ideally should transmit. This extra absorption results in less effective reproduction by the final image of one or more colors present in the original object. In particular, magenta image forming dyes typically exhibit significant absorption in the blue region.

Accordingly, there is a continuing search for new image forming dyes and, concomitantly, for new processes for preparing the dyes. The present application relates to a novel process for preparing aralkyl derivatives of xanthene dyes.

SUMMARY OF THE INVENTION

It is therefore the object of this invention to provide a novel process for preparing aralkyl derivatives of xanthene dyes.

It is another object to provide such a process wherein previously formed xanthene dyes are aralkylated.

A further object is to provide such a process which is relatively rapid.

Still another object is to provide such a process which gives a substantially pure product.

Yet another object is to provide a process for preparing dye developers which are useful in photography.

BRIEF SUMMARY OF THE INVENTION

These and other objects and advantages are accomplished in accordance with the invention by providing a process wherein a xanthene dye is initially reacted with a strong base such as an alkali metal hydroxide to form a salt of the dye and subsequently reacting the dye salt with an aralkyl compound. The reactions may be carried out in various solvents such as, for example, dimethylformamide, dimethylsulfoxide, 2-methoxyethyl ether and the like. In a preferred embodiment the process of the invention is used in the preparation of xanthene compounds which are useful as dye developers in photography.

DESCRIPTION OF THE PREFERRED EMBODIMENTS

The process of the invention proceeds according to the following general reaction scheme:

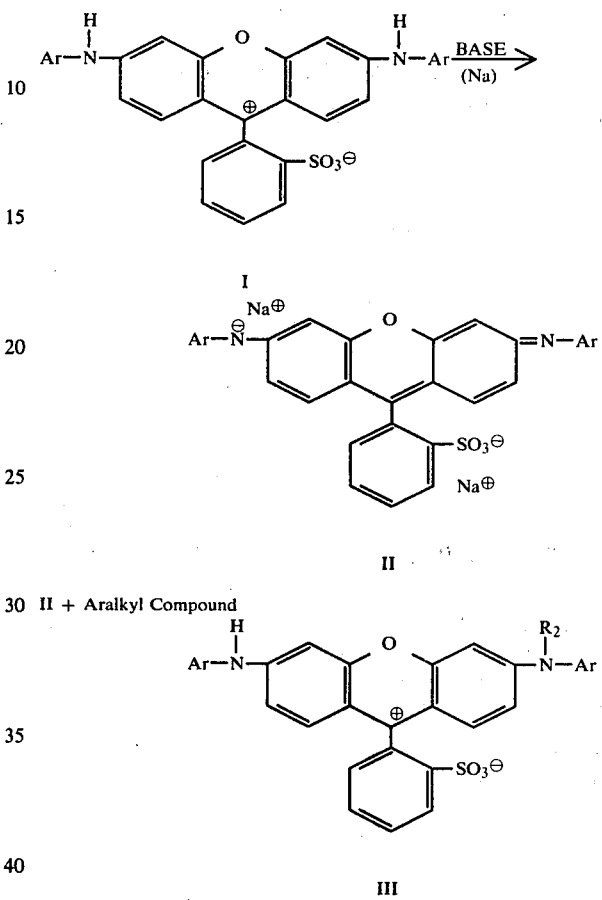

wherein Ar is an aromatic radical such as, for example, a radical of benzene or naphthalene including aromatic radicals having substituents such as halogens and alkyl groups appended thereto and aromatic radicals which are linked to blocked silver halide developing moieties through alkylene linkages; and $R_2$ is aralkyl represented by the formula

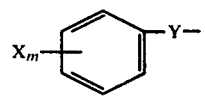

wherein X is $OR_3$ where $R_3$ is alkyl having from 1 to 3 carbon atoms or benzyl and m is an integer of from 0 to 2; and Y is $C_nH_{2n}$ where n is an integer of from 1 to 5.

In one preferred embodiment of the invention Ar is

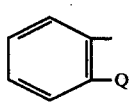

where Q is a halogen, preferably bromine. In another preferred embodiment, Ar is

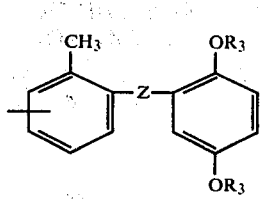

wherein Z is an alkylene linkage having from 2 to 6 carbon atoms and $R_3$ is as previously defined. In a particularly preferred embodiment Ar is

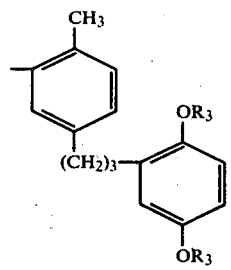

It has been found that only one of the nitrogen atoms will be aralkylated under relatively mild reaction conditions, for example, at a temperature below about 80°–90° C. and required amounts of reactants, as will be illustrated in the Examples. The second nitrogen atom, as is apparent from the general reaction sequence illustrated above, has a hydrogen atom attached thereto. In a preferred embodiment of the invention the second nitrogen atom is subsequently methylated by reaction with a methylating agent.

The base may be any suitable strong base which is capable of removing the hydrogen atoms from the nitrogen atoms. Typical suitable bases which may be used include alkali metal bases such as sodium hydroxide, sodium hydride, sodium ethoxide, potassium tertiary butoxide and the like. Any appropriate solvent may be used including, for example, organic solvents such as dimethylformamide, dimethylsulfoxide, 2-methoxyethyl ether (Diglyme) and the like. The selection of an appropriate solvent in a particular instance will be dependent primarily upon the base which is being used.

Typical suitable aralkyl compounds which may be employed to react with the xanthene dye salt (II) to give the desired product (III) are represented by the formula Preferred aralkyl compounds are represented by the formula

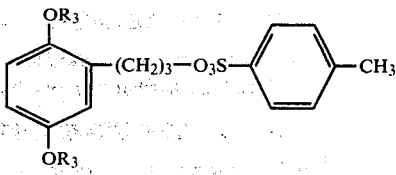

A particularly preferred compound is represented by the formula

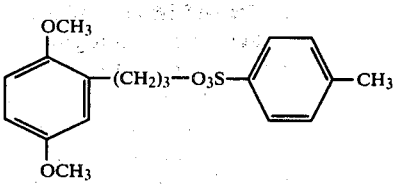

Where it is desired to methylate the second nitrogen atom of the xanthene compound any suitable methylating agent may be used such as, for example, methyl iodide, dimethyl sulfate, methyl tosylate and the like.

The xanthene dye starting material (I) can be made by processes which are well known in the art and accordingly discussion of such processes is not required here. Generally, in the process of the invention the xanthene dye and the base are initially combined in an appropriate solvent, preferably in an inert atmosphere, and reacted to form a salt of the dye. The aralkyl compound is then added to the reaction mixture and reacts with the dye salt to form the product (III).

In a preferred embodiment of the invention the aralkylated dye compound (III) includes blocked silver halide developer groups and is converted to a dye developer which is particularly useful in diffusion transfer film units of the type disclosed in U.S. Pat. Nos. 2,983,606; 3,415,644 and 3,647,437 by various known techniques such as reaction with boron tribromide to deblock the silver halide developing groups.

The invention will now be described further in detail with respect to specific preferred embodiments thereof by way of examples, it being understood that these are intended to be illustrative only and the invention is not intended to be limited to the materials, conditions, process parameters, etc., recited therein.

EXAMPLE I 10 g of a xanthene dye represented by the formula

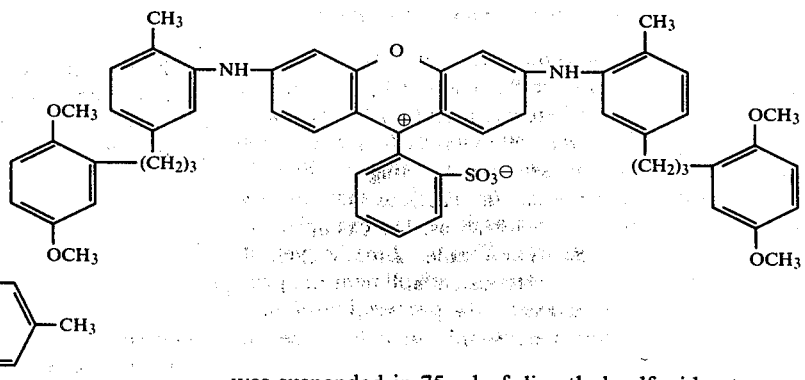

was suspended in 75 ml of dimethyl sulfoxide at room temperature under nitrogen gas. To this suspension there was added 1.8 g of a 50% sodium hydride dispersion in oil and the mixture stirred for 30 minutes at room temperature. A blue solution developed. To the solution there was added 10 g of a tosylate compound represented by the structural formula

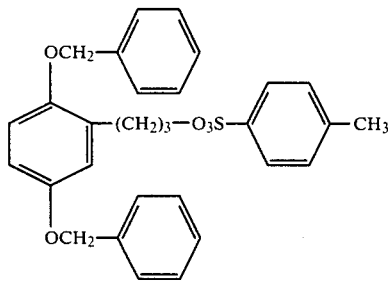

and the solution stirred for 3 hours at room temperature. TLC on silica gel with 5/95 methanol/methylene chloride, by volume, showed that none of the dye intermediate remained. Methyl iodide (2 ml) was added and the mixture was stirred for one hour. TLC showed that the reaction was complete. The reaction mixture was poured into 1 liter of water containing 1 ml of conc. HCl and the precipitate was filtered off. The precipitate was placed back into water, stirred well, collected by filtration and vacuum dried to give 14.0 g. The product was dissolved in 400 ml of methylene chloride and 125 g of silica gel added to the solution. The stirred mixture was placed in a sintered glass funnel and filtered while washing with methylene chloride. The dye was then extracted with 5/95 methanol/methylene chloride, by volume, and evaporated to dryness. The dye is represented by the structural formula and a magenta precipitate formed. The precipitate was collected by filtration, washed well with methylene chloride and vacuum dried at 80° C. to give 9.0 g of solid. The solid was dissolved in methanol containing several drops of conc. HCl, refluxed, and poured into 1000 ml of ether. The precipitate was collected by filtration and dried to give 3.8 g of product.

The 3.8 g sample was placed on 60 g of sea sand with methanol. The mixture was placed in a steel column and an additional 250 g of sea sand were added. The column was placed on line on a high pressure chromatography unit and washed with a succession of solvents as follows (parts are by volume):

1 liter methylene chloride
2 liters 1/99 methanol/methylene chloride
4 liters 2/98 methanol/methylene chloride
4 liters 3/97 methanol/methylene chloride
12 liters 5/95 methanol/methylene chloride
3 liters 6/94 methanol/methylene chloride The appropriate solvent fractions as determined by thin layer chromatography were collected and evaporated to give 1.8 g of the dye developer.

TLC of the material showed traces of impurities. The sample was again placed on 60 g of sea sand and placed back in the steel column (which was first washed with 9/91 methanol/methylene chloride, by volume, and then with methylene chloride). The column was washed with a succession of solvents as follows (parts are by volume):

1 liter methylene chloride
3 liters 2/98 methanol/methylene chloride
3 liters 3/97 methanol/methylene chloride
1 liter 4/96 methanol/methylene chloride
10 liters 4/96 methanol/methylene chloride
3 liters 6/94 methanol/methylene chloride The appropriate solvent fractions as determined by thin

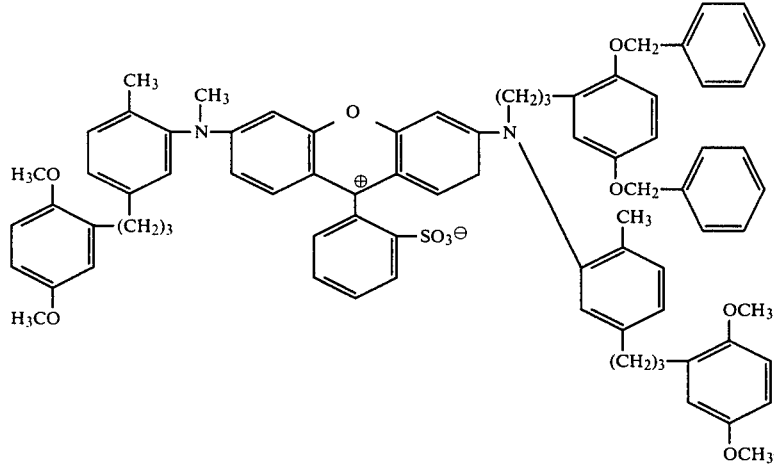

EXAMPLE II

A dye developer was prepared by initially adding, dropwise over a 45 minute period, a solution of 5.0 g of the dye prepared as described in Example I in 100 ml of methylene chloride to a stirred solution of 15 ml of boron tribromide in 500 ml of methylene chloride, under nitrogen and cooled to 5° C. The magenta solution was allowed to warm to room temperature. TLC on silica gel showed two spots. A sample of the solution was heated to reflux with no apparent change in the TLC results. Water was added dropwise to the solution layer chromatography were collected and evaporated to give 1.7 g of the dye developer which was shown to be pure by TLC. The product exhibited maximum absorption in methyl cellosolve at 553 nm, $\epsilon = 117,500$. An NMR spectrum of the product confirmed the structure.

The dye developer is disclosed and claimed in copending patent application Ser. No. 32,876 filed on even date herewith now abandoned and replaced by continuation-in-part applications Ser. Nos. 143,290 and 143,438, both filed Apr. 24, 1980.

EXAMPLE III

A slurry of 0.5 g of the starting xanthene dye described in Example I in 50 ml of dry tetrahydrofuran was added to 1.0 g of sodium hydride (50% dispersion in oil) and 25 ml of dry tetrahydrofuran. A dark red solution was formed. The solution was brought to reflux. After about 15 minutes the solution changed to a dark blue color. Benzyl chloride (0.5 g) was added to the solution and the refluxing continued. After 1 hour an additional 0.5 g of benzyl chloride was added to the refluxing solution.

The reaction was monitored by thin layer chromatography using 10/90 methanol/methylene chloride (vol/vol) as the eluent. The starting material was slowly converted into the mono-benzylated material. The reaction was complete after 1½ hours. Only a trace of the bisbenzylated material was formed.

An aliquot of the reaction mixture (taken after 1½ hours) was treated with methyl iodide at room temperature. Thin layer chromatographic analysis indicated complete conversion to the mono-methyl, mono-benzyl material in about 15 minutes.

EXAMPLE IV

A solution of 0.25 g of a xanthene compound represented by the formula

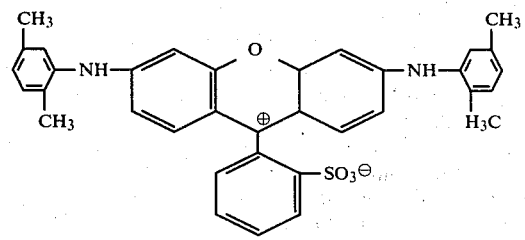

in 15 ml of dry dimethylsulfoxide was prepared under nitrogen at room temperature. To this magenta solution there was added 0.08 g of 85% potassium hydroxide pellets which had been ground to powder. A blue color developed within minutes. The solution was stirred for 15 minutes and then 0.44 g of the tosylate compound described in Example I was added. The mixture was stirred over the weekend and a red colored solution formed. The solution was poured into 400 ml of acidic water and the magenta precipitate was filtered off. The precipitate was vacuum dried. Analysis of the product by thin layer chromatography on silica gel using 9/1 methylene/chloride/methanol (v/V) showed a major amount of the desired product with minor amounts of other reaction products. The product exhibited a $\lambda max = 545$ nm in methanol and is represented by the formula

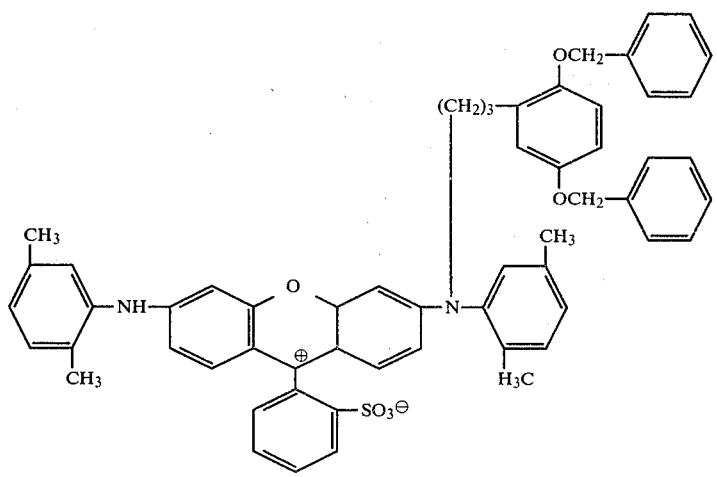

To 20 ml of dimethylsulfoxide at room temperature and under nitrogen there was added 1 g of the above product and 0.2 g of powdered 85% potassium hydroxide pellets to form a magenta solution. The solution was stirred for 15 minutes, 1 ml of dimethylsulfate added and the mixture stirred overnight at room temperature. Thin layer chromatographic analysis indicated that little reaction had taken place.

Additional powdered 85% potassium hydroxide (1 g) was added and an immediate reaction took place as evidenced by a color change. The mixture was stirred overnight and then poured into 500 ml of acidic water. A purple precipitate was collected by filtration and dried to yield 1.0 g of a xanthene compound represented by the structure

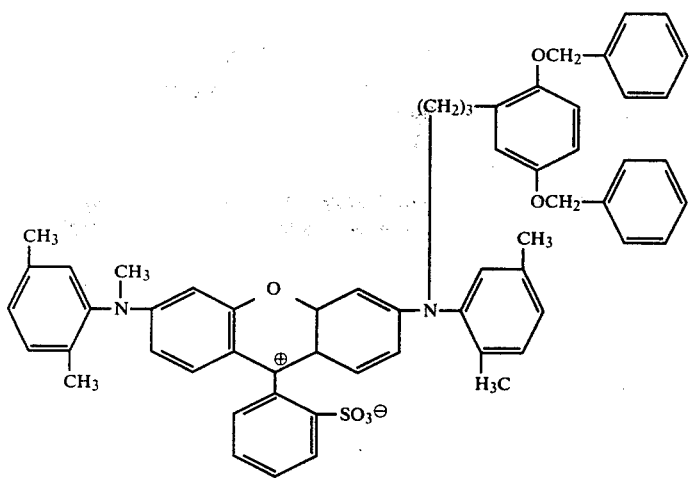

Thin layer chromatographic analysis of the product showed one major spot. The product exhibited $\lambda\text{max} = 549$ nm in ethanol.

Although the invention has been described with respect to specific preferred embodiments, it is not intended to be limited thereto but rather those skilled in the art will recognize that variations and modifications may be made therein which are within the spirit of the invention and the scope of the appended claims.

What is claimed is:

1. A process for preparing a xanthene dye comprising reacting a compound represented by the formula

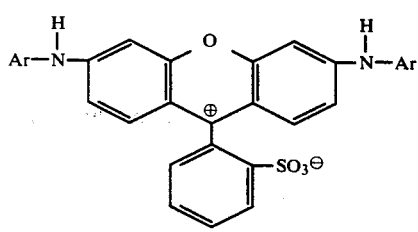

wherein Ar is a radical of benzene or naphthalene, with a base in a solvent to form a salt of compound I and reacting said salt with an aralkyl compound to form a xanthene dye represented by the formula

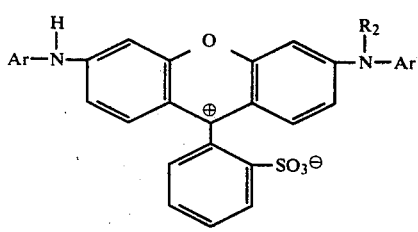

wherein $R_2$ is aralkyl represented by the formula

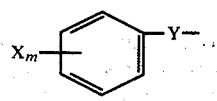

wherein X is $OR_3$ where $R_3$ is alkyl having from 1 to 3 carbon atoms or benzyl and m is an integer of from 0 to 2; and Y is $C_nH_{2n}$ where n is an integer of from 1 to 5.

2. The process as defined in claim 1 wherein said base is an alkali metal hydroxide.

3. The process as defined in claim 1 and further including the step of reacting said compound II with a methylating agent to form a compound represented by the formula

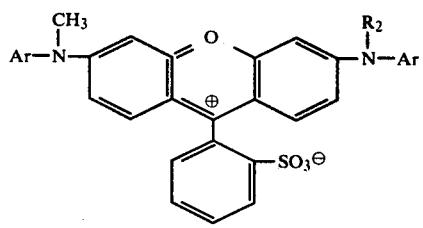

4. The process as defined in claim 3 wherein Ar is represented by the formula

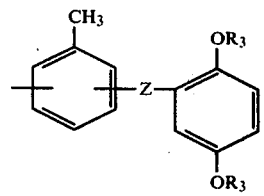

wherein Z is an alkylene linkage having from 2 to 6 carbon atoms.

5. The process as defined in claim 4 wherein Z is an alkylene linkage having 3 carbon atoms.

6. The process as defined in claim 5 wherein Ar is represented by the formula

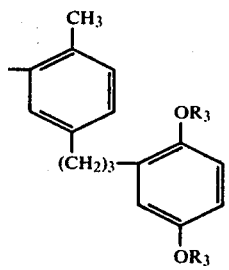

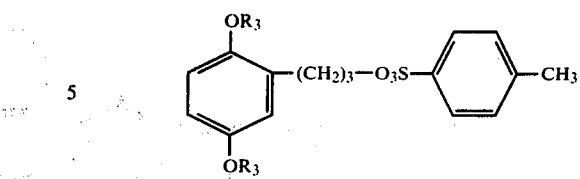

9. A process for preparing a xanthene dye comprising reacting a compound represented by the formula

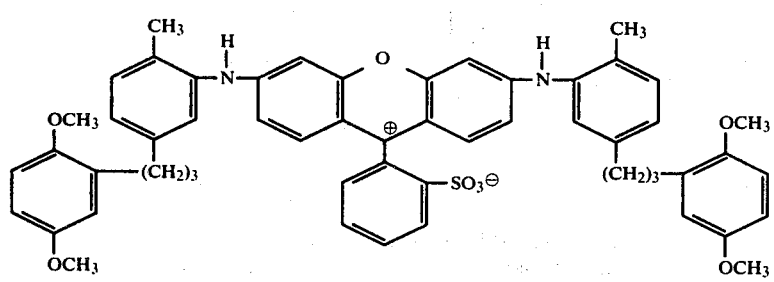

7. The process as defined in claim 1 wherein said aralkyl compound is represented by the formula

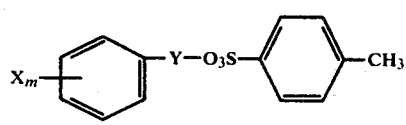

8. The process as defined in claim 7 wherein said aralkyl compound is represented by the formula with a base in a solvent to form a salt of compound I and reacting said salt with an aralkyl compound represented by the formula

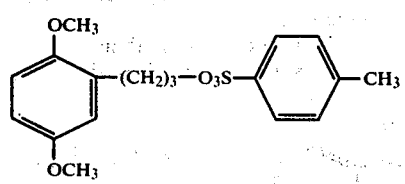

to form a xanthene dye represented by the formula

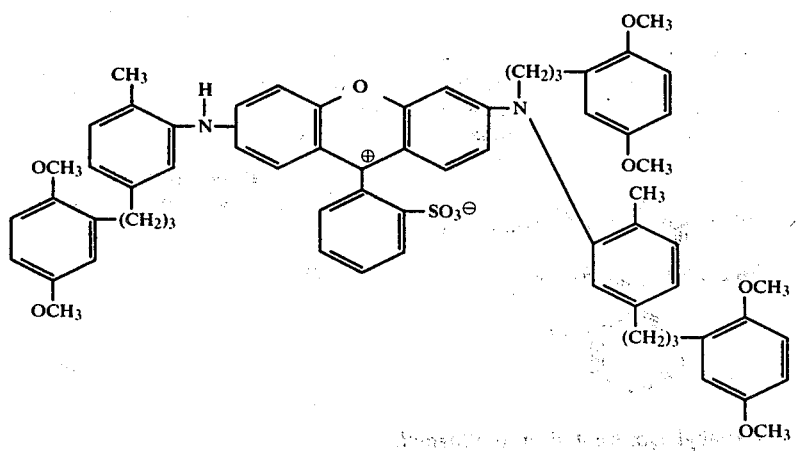

II

10. The process as defined in claim 9 and further including reacting said xanthene dye II with a methylating agent to form a xanthene dye represented by the formula

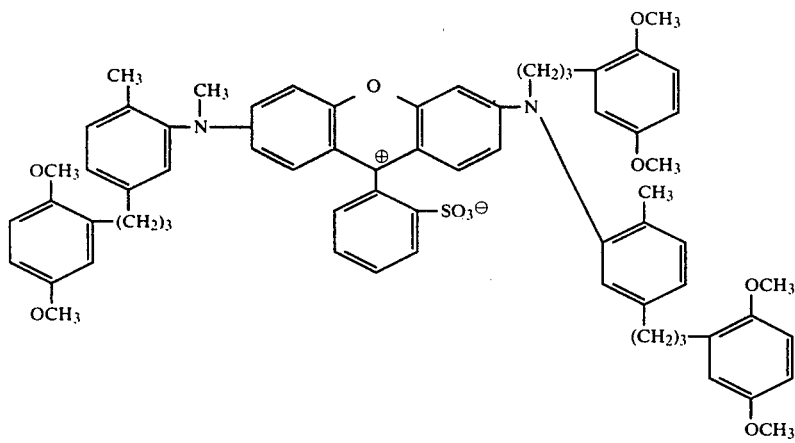

11. The process as defined in claim 10 and further including the step of converting said xanthene dye III to a dye developer represented by the formula

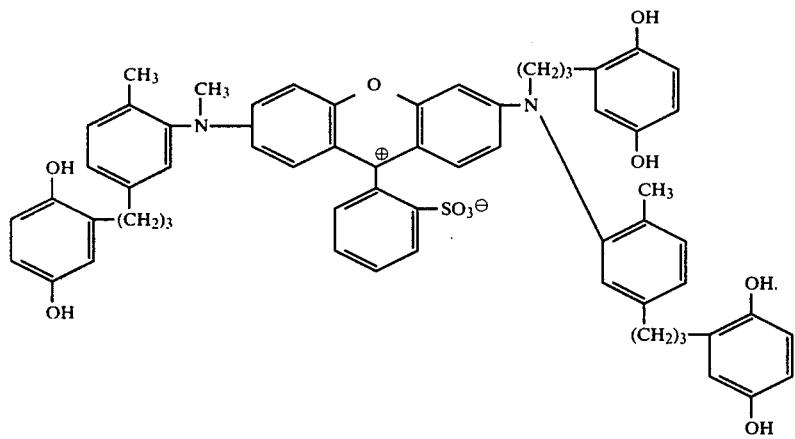

12. The process as defined in claim 11 wherein said base is an alkali metal hydroxide.

13. The process as defined in claim 11 wherein said base is a member of the group consisting of potassium tertiary butoxide, sodium hydride and potassium hydroxide.

14. The process as defined in claim 13 wherein said solvent is 2-methoxyethyl ether.

15. The process as defined in claim 1 wherein said base is a member of the group consisting of potassium tertiary butoxide, sodium hydride and potassium hydroxide.